US011185579B2

(12) United States Patent
O'Connell et al.

(10) Patent No.: US 11,185,579 B2
(45) Date of Patent: Nov. 30, 2021

(54) ORAL VACCINE AGAINST RUMINANT RESPIRATORY DISEASE COMPRISING POLYVINYLPYRROLIDONE

(71) Applicant: Intervet Inc., Madison, NJ (US)

(72) Inventors: Kevin O'Connell, Omaha, NE (US); Subramaniam Vaidyanathan, Lenexa, KS (US); Brad Eddy, Saint Joseph, MO (US)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 16/468,187

(22) PCT Filed: Dec. 11, 2017

(86) PCT No.: PCT/EP2017/082139

§ 371 (c)(1),
(2) Date: Jun. 10, 2019

(87) PCT Pub. No.: WO2018/108772

PCT Pub. Date: Jun. 21, 2018

(65) Prior Publication Data

US 2019/0381161 A1 Dec. 19, 2019

Related U.S. Application Data

(60) Provisional application No. 62/432,803, filed on Dec. 12, 2016.

(30) Foreign Application Priority Data

Jan. 11, 2017 (NL) ..................................... 2018155

(51) Int. Cl.

| | |
|---|---|
| ***A61K 39/102*** | (2006.01) |
| ***A61K 9/00*** | (2006.01) |
| ***A61K 9/19*** | (2006.01) |
| ***A61K 47/32*** | (2006.01) |
| ***A61K 39/00*** | (2006.01) |

(52) U.S. Cl.

CPC .......... *A61K 39/102* (2013.01); *A61K 9/0095* (2013.01); *A61K 9/19* (2013.01); *A61K 47/32* (2013.01); *A61K 2039/522* (2013.01); *A61K 2039/54* (2013.01); *A61K 2039/542* (2013.01); *A61K 2039/552* (2013.01)

(58) Field of Classification Search

None

See application file for complete search history.

(56) References Cited

U.S. PATENT DOCUMENTS

| | | | |
|---|---|---|---|
| 6,982,088 | B2 | 1/2006 | Francon et al. |
| 9,393,298 | B2 | 7/2016 | Buchanan et al. |
| 2006/0171960 | A1 | 8/2006 | Chu et al. |

FOREIGN PATENT DOCUMENTS

| | | | |
|---|---|---|---|
| WO | 1993016680 | A1 | 9/1993 |
| WO | 1994020070 | A1 | 9/1994 |
| WO | 1999015670 | A1 | 1/1999 |
| WO | 2000050078 | A1 | 8/2000 |
| WO | 2002028362 | A2 | 4/2002 |
| WO | 2004064776 | A2 | 8/2004 |
| WO | 2005000330 | A1 | 1/2005 |
| WO | 2007035455 | A2 | 3/2007 |
| WO | 2014074817 | A2 | 5/2014 |
| WO | 2014140239 | A1 | 9/2014 |
| WO | 2015124594 | A1 | 8/2015 |

OTHER PUBLICATIONS

Lal et al (Vaccine, 31:4759-4764, 2013).*

European Search report for NL2018155, dated Apr. 21, 2017, 9 pages. (Cover letter is in Dutch, Search report and Written Opinion in English).

International Search Report for application PCTEP2017082139, dated Jan. 30, 2018, 3 Pages.

Angen, Taxonomic relationships of the [Pasteurella] haemolytica complex as evaluated by DNA-DNA hybridizations and 16S rRNA sequencing with proposal of *Mannheimia haemolytica* gen. nov., comb. nov., *Mannheimia glucosida* sp. nov., *Mannheimia ruminalis* sp. nov., International Journal of Systematic Bacteriology, 1999, 67-86, 49.

Buhler (in: 'Polyvinylpyrrolidone excipients for pharmaceuticals', ISBN 3-540-23412-8, Springer Berlin, 2005) (Buhler, supra: p. 120, section 2.4 9.2) and (Buhler, supra: p. 124, section 2.4 9.9).

Chengappa, M.M., Improved Method for Obtaining Streptomycin-Dependent Mutants from Pasteurella multocida and pasteurella haemolytica, Using N-Methyl-N'-Nitro-N-Nitrosoguanidine, Am. J. Vet. Res., 1979, 449-450, 40.

Chung, Jing Yeng, The capsule biosynthetic locus of Pasteurella multocida A:1, FEMS Microbiology Letters, 1998, 289-296, 166.

Griffin, Dee, Bovine Pasteurellosis and Other Bacterial Infections of the Respiratory Tract, Vet. Clin. Food Animals, 2010, 57-71,26.

Grissett, G.P., Structured Literature Review of Responses of Cattle to Viral and Bacterial Pathogens Causing Bovine Respiratory Disease Complex, Journal of Veterinary Internal Medicine, 2015, 770-780, 29.

Jericho, K.W.F. and Langford, E.V., Aerosol vaccination of calves with Pasteurella haemolytica against experimental respiratory disease, Can. J comp. Med., Jul. 1982, pp. 287-292, vol. 46.

Suzuki, M., Effect of suspending media on freeze-drying and preservation of vaccinia virus, J. Hyg., Camb., 1970, 29-41, 68.

* cited by examiner

*Primary Examiner* — Brian Gangle

(74) *Attorney, Agent, or Firm* — Michael D. Davis

(57) ABSTRACT

The present invention relates to an oral vaccine against respiratory disease in ruminants, comprising live attenuated *Mannheimia haemolytica* bacteria and a Polyvinylpyrrolidone (PVP). The addition of PVP significantly improves the protective effect of vaccination on lung scores after a challenge infection. Further the PVP allows vaccination by a method of mass administration, such as by oral route via a drink. In addition the invention relates to methods for the preparation of such a vaccine, to methods for the vaccination of ruminants employing such a vaccine, and to medical uses of a composition comprising *M. haemolytica* bacteria.

20 Claims, No Drawings

ORAL VACCINE AGAINST RUMINANT RESPIRATORY DISEASE COMPRISING POLYVINYLPYRROLIDONE

CROSS-REFERENCE TO RELATED APPLICATIONS

This application is a national stage entry under 35 U.S.C. § 371 of PCT/EP2017/082139, filed on Dec. 11, 2017, which claims priority to NL Application 2018155, filed on Jan. 11, 2017 and to U.S. Application 62/432,803, filed Dec. 12, 2016, the content of PCT/EP2017/082139 is hereby incorporated by reference in its entirety.

The present invention relates to the field of veterinary vaccinology; specifically the invention relates to an oral vaccine against respiratory disease in ruminants, comprising live attenuated *Mannheimia haemolytica* bacteria. In addition the invention relates to methods for the preparation of such a vaccine, to methods for the vaccination of ruminants employing such a vaccine, and to medical uses of a composition comprising *M. haemolytica* bacteria.

In the animal husbandry of ruminants, one of the main veterinary problems is respiratory disease. This is a complex syndrome of affections with serious negative effects on animal welfare and on economy of operation. Several causes are considered to be relevant in ruminant respiratory disease (RRD): at the basis is infection by one or more bacteria and viruses, which is facilitated and aggravated by environmental stress factors. Such stress can resort from housing conditions such as heat, thirst, crowding, poor ventilation (dust and ammonia); from social factors such as weaning, and co-mingling into new groups; as well as from handling and transportation. This is why RRD is often called ‘shipping fever pneumonia’.

The pathogens involved are bacteria, among others: *Mannheimia haemolytica, Pasteurella multocida, Mycoplasma bovis*, and *Histophilus somni*; and viruses, amongst others: bovine coronavirus (BCV), parainfluenza-3 (PI3) virus, bovine respiratory syncytial virus (BRSV), bovine viral diarrhoea virus (BVDV) and bovine herpes virus 1 (BHV1), which causes infectious bovine rhinotracheitis (IBR). Some reviews on the respiratory disease complex in bovines are: D. Griffin (2010, Vet. Clin. Food Animals, vol. 26, p. 57-71), and Grissett et al. (2015, J. Vet. Intern. Med., vol. 29, p. 770-780).

Several veterinary treatments are available to prevent or mitigate RRD, often combinations are being used of antibiotics and of vaccines for the viral- and bacterial pathogens.

Of the commercial vaccines for bacterial pathogens involved in RRD, most are inactivated-adjuvated vaccines with antigens of *M. haemolytica* and *P. multocida*, in the form of bacterins (inactivated bacteria) or toxoids (de-toxified toxins). Such vaccines are intended for parenteral injection by intramuscular or subcutaneous route. For example: Bovipast™ and Ovipast™ (Merck Animal Health), Rispoval™ (Zoetis), Presponse™ (Boehringer Ingelheim), and Respishield™ (Merial). Only few vaccines against bacterial RRD comprise live attenuated bacteria. Reason is that such live attenuated bacterial vaccines cannot easily be combined with the preventive use of antibiotics. Examples are: Onset™, ONCE™, Vista™, and Respavir™ (all from Merck Animal Health). These live attenuated vaccines are administered either by subcutaneous- or intranasal route. Both these routes are quite stressful to the animal, because the intranasal route typically requires the physical restraint of the animal, and especially its head; either by a human or by mechanical means.

Further, the intranasal administration of a liquid is apparently very unpleasant. Also, vaccine applied intranasally can be sneezed out again, so that the animal did not receive a full dose of vaccine. Consequently there is an urgent need in this field for a live attenuated bacterial vaccine against RRD that can be administered in a more convenient and less stressful way.

Of the bacterial pathogens involved in RRD, *M. haemolytica* is the major cause of disease. While being a commensal of the upper respiratory tract in ruminants, it can become the principal bacterial pathogen associated with pneumonic Pasteurellosis in RRD if an opportunity arises. Typical clinical symptoms of disease are fever, depression, and increase of respiration frequency. Histopathological signs are characteristic lung lesions such as necrosis, thrombosis, and exudation.

*M. haemolytica* is a member of the Pasteurellaceae family, and was previously called *Pasteurella haemolytica* (Angen et al., 1999, Int. J. Syst. Bacteriol., vol. 49, p. 67-86).

The Pasteurellaceae are Gram-negative, rod-shaped, non-motile, and facultative anaerobes. Pasteurellaceae are commonly sub-divided into serotypes based on their capsular antigen. The most prominent serotypes of *M. haemolytica* in RRD are A1 and A6. The main virulence factors are the capsular polysaccharide and the leukotoxin. Live attenuated strains of *M. haemolytica* have been described, comprising different attenuating mutations, for instance in: Chengappa & Carter (1979, Am. J. Vet. Res., vol. 40, p. 449-450), WO 1999/015670, and WO 2004/064776.

A Polyvinylpyrrolidone (PVP) is a synthetic polymer which has been known since the 1930's and is widely used for a variety of purposes: in foodstuffs as a stabiliser (E1201); in technical products, e.g. in paint or glue; and in cosmetics and pharmaceuticals as a binder, thickener, emulsifier or disintegrant.

WO 94/20070 is titled ‘Polymeric mucoadhesives in the delivery of immunogens at mucosal surfaces’. It presents a list of compounds ‘considered to act as mucoadhesives’, among which is PVP. ’070 prefers the use of carboxymethylcellulose and an adjuvant. The only antigen tested is inactivated H3N2 influenza virus, which is administered to mice by oral- or intragastric route. Not all experiments showed protection, and the samples that did show seroconversion were later found to be bacterially contaminated. This was then assigned to be a ‘bacterial adjuvant’. ’070 concludes that the viral antigen, with mucoadhesive but without a bacterial adjuvant was unable to provide a significant immune response by oral immunisation (’070, page 24, $9^{th}$-$3^{rd}$ line from the bottom).

WO 00/50078 is titled ‘Use of bioadhesives and adjuvants for the mucosal delivery of antigens’, and aims to develop an intranasal vaccine against influenza for humans. ’078 lists PVP and hydroxy-propyl-methyl cellulose (HPMC) as bioadhesives. The bioadhesive is preferred to be a microsphere with the antigen adsorbed on, or entrapped within the spheres. The only experiment described applies intranasal administration of Influenza HA antigen to rabbits, using a bacterial toxin as adjuvant, and polycarbophil, carbopol, or HPMC as bioadhesive.

WO 2005/00330 describes an acapsular deletion mutant of *P. multocida*, to be used as a live attenuated vaccine administered via the feed or drinking water. ’330 describes immunisation of turkeys by intramuscular injection, and of calves by subcutaneous route, or by oral route via the feed. No use of or need for any other excipient is described or suggested.

Bühler (in: 'Polyvinylpyrrolidone excipients for pharmaceuticals', ISBN 3-540-23412-8, Springer Berlin, 2005) describes the suitability of PVP as bioadhesive for the delivery of pharmaceutical compounds to dermal and mucosal surfaces (Bühler, supra: p. 120, section 2.4.9.2). However the suitability of PVP for use in mouthwashes etc. is described to derive from its reduction of the adherence of oral bacteria to tooth enamel, hence its use as microbial anti-adherent agent (Bühler, supra: p. 124, section 2.4.9.9).

WO 93/16680 also describes the microbial anti-adherence effect of PVP in dentifrices.

It is an object of the present invention to overcome a disadvantage in the prior art, and to accommodate to a need in the field by providing a live attenuated bacterial vaccine against ruminant respiratory disease that can be administered by a more convenient and less stressful route of administration, while still inducing an effective immune-protection.

One common method of mass application of vaccines is by oral route. However when the inventors attempted the straightforward oral application of existing live attenuated bacterial vaccines prescribed for administration by intranasal route, this was not successful. While effective for *P. multocida* bacteria, but surprisingly the oral route was no success for the closely related *M. haemolytica*. This even when doses of the bacterium were applied that were near the maximum levels that can be produced (above 10^9 bacteria per animal dose), even with rich culture media and state of the art industrial systems for bacteriological production. The inventors then attempted to concentrate an *M. haemolytica* culture, but this only reduced the final titre of live bacteria. The inventors had no indications from the prior art on how to overcome this problem.

Surprisingly it was found that the object can be met, and consequently one or more disadvantages of the prior art can be overcome, by providing an effective vaccine for RRD comprising live attenuated *Mannheimia haemolitica* bacteria, that can be administered by oral route. This was reached by the addition of a Polyvinylpyrrolidone to the vaccine.

The advantageous effect of the novel vaccine is that its administration by oral route, especially when applied as a drink or with the feed, allows the cheap and effective mass vaccination of animals. This no longer requires an additional handling of the animals and so reduces unnecessary stress to the animal, and in addition saves considerably on expenses for labour and veterinary services. Because stress is such an important factor in RRD, therefore the reduction of stress to the animal by vaccination using a method of mass administration helps to reduce onset of RRD.

PVP, in the concentration range in which it was found to be effective, was found to be non-toxic to the live attenuated *M. haemolytica* bacteria.

It is currently not known why the addition of a PVP enables the administration of a live attenuated *M. haemolytica* by oral route. Although the inventors do not want to be bound by any theory or model that might explain these observations, they speculate that a PVP in some way or other associates with the bacteria in the vaccine, which allows these bacteria to more effectively establish a colonisation of the upper respiratory tract and/or results in a better exposure of these bacteria to the immune system.

Therefore in one aspect the invention relates to an oral vaccine against respiratory disease in ruminants, the vaccine comprising live attenuated *Mannheimia haemolitica* bacteria and a pharmaceutically acceptable carrier, wherein the vaccine also comprises Polyvinylpyrrolidone (PVP).

For the invention "oral" refers to a route of administration to a target ruminant via the oral cavity of the animal, typically: via the mouth, also known as: per os. Inter alia this includes routes of administration that are termed: buccal, (sub)lingual, (sub)labial, laryngeal, oro-pharyngeal, tonsilar, or oro-mucosal. Further this also refers to an indirect administration to the oral cavity, such as by administration to the muzzle area of a ruminant; the animal's natural tendency to clean itself by licking, or even by licking another ruminant, will then cause the inoculum to reach the oral cavity.

In practice oral refers to ingestion of vaccine by some way of eating or drinking, but may also comprise spray or nebulisation of a liquid or a powder.

A "vaccine" is well known to be a composition that has a medical effect. A vaccine comprises an immunologically active component, and a pharmaceutically acceptable carrier. The 'immunologically active component', is one or more antigenic molecule(s), here: live *M. haemolytica* bacteria, that are recognised by the immune system of a target, and induce a protective immunological response. The response may originate from the targets' innate- and/or from the acquired immune system, and may be of the cellular- and/or of the humoral type.

A vaccine generally is efficacious in reducing the level or the extent of an infection by the target pathogen, for example by reducing the load or shortening the duration of the replication of pathogenic *M. haemolytica* bacteria in a host ruminant.

Also, or possibly as a results thereof, a vaccine generally is effective in reducing or ameliorating the (clinical) symptoms of disease that may be caused by such infection or replication, or by the animal's response to that infection or replication.

The effect of an oral vaccine according to the invention is the prevention or reduction in ruminants of an infection by a pathogenic *M. haemolytica*, and/or of one or more signs of respiratory disease that are associated with such infection or replication. Such (clinical) signs are: fever, increased respiration rate, nasal discharge, and several types of inflammatory affections to the lungs causing typical lesions. Consequently, the oral vaccine according to the invention is an aid in the reduction of respiratory disease caused by *M. haemolytica*, as is e.g. detectable in reduction of the number and/or the severity of lung lesions caused by *M. haemolytica*.

Such an *M. haemolytica* vaccine may colloquially also be referred to as a vaccine 'against' *M. haemolytica*, a vaccine 'against' pneumonic Pasteurellosis, or as an '*M. haemolytica* vaccine'.

Embodiments and details of an oral vaccine according to the invention, its production, and its uses will be described herein below.

"Respiratory disease" for the invention refers to any disease of a ruminants' respiratory tract. Typically this is a consequence of infection with a pathogenic *M. haemolytica* bacteria, commonly in combination with infection by one or more bacteria or viruses. For a description see veterinary handbooks such as: "The Merck veterinary manual" (10th ed., 2010, C. M. Kahn edt., ISBN: 091191093X). Examples of such a disease are: shipping fever, or pneumonic Pasteurellosis.

A "ruminant" for the invention is an animal assigned to the suborder Ruminantia, and/or an animal applying the process of rumination to digest its feed.

The terms "live" and "attenuated" for the invention refer to bacteria that are alive, meaning replicative, and that have a reduced capacity to induce infection or disease in a particular host, as compared to un-attenuated, more pathogenic strains of the bacterium. A synonym is: modified-live. The effect of the attenuation is that the bacterium can still replicate in a target animal and so display relevant antigens to the targets' immune system, but without itself causing (serious) disease to the target. This effectively protects the target against (the consequences of) an infection with an un-attenuated version of the bacterium.

The use of live attenuated bacteria in vaccination is known since the 1880's. Stably attenuated bacteria will carry a genetic mutation that induces a loss in replicative or infective capacity, such as a mutation to their external organelles, their coat or capsule, to the expression of a virulence factor, or to their internal organisation. An attenuated bacterium can be generated in vitro in a wide variety of ways, such as through a method of induced mutation, either directed or a-specific. Examples are subsequent passaging (in vivo or in vitro); use of mutagens such as chemicals or ionising radiation; or recombinant DNA technology. Also a bacterium can be considered to be attenuated upon infection of a particular target species, while being fully pathogenic when infecting its natural host species.

"*M. haemolytica*" are bacteria from the Pasteurellaceae family. They display the characterising features of their taxonomic group-members such as the morphologic, genomic, and biochemical characteristics, as well as the biological characteristics such as physiologic, immunologic, or pathologic behaviour. As is known in the field, the classification of micro-organisms is based on a combination of such characterising features. The scope of the invention therefore also includes *M. haemolytica* bacteria that are sub-classified therefrom in any way, for instance as a subspecies, strain, isolate, genotype, variant, subtype, serotype, or subgroup and the like.

It will be apparent to a skilled person that while a particular *M. haemolytica* bacterium for the present invention may currently be classified in a specific species and genus, such a taxonomic classification can change in time as new insights may lead to reclassification into a new or different taxonomic group. This applies in particular to *M. haemolytica* which was previously classified as *Pasteurella haemolytica*. Such reclassification does not change the micro-organism itself, its genetic or antigenic repertoire, or the level of genetic relatedness to other bacteria, but only its scientific name or classification. Therefore such re-classified bacteria remain within the scope of the invention.

A "pharmaceutically acceptable carrier" is for example a liquid such as water, physiological salt solution, or phosphate buffered saline solutions. In a more complex form the carrier can e.g. be a buffer comprising further additives, such as stabilisers or preservatives.

The term "comprises" (as well as variations such as "comprise", "comprising", and "comprised") as used herein, intends to refer to all elements, and in any possible combination conceivable for the invention, that are covered by or included in the text section, paragraph, claim, etc., in which this term is used, even if such elements or combinations are not explicitly recited; and not to the exclusion of any of such element(s) or combinations.

Therefore any such text section, paragraph, claim, etc., can therefore also relate to one or more embodiment(s) wherein the term "comprises" (or its variants) is replaced by terms such as "consist of", "consisting of", or "consist essentially of".

A "Polyvinylpyrrolidone" is a synthetic polymer of 1-vinyl-2-pyrrolidinone units. The compound has CAS number 9003-39-8, is abbreviated as PVP, and has several synonyms, such as: Polyvidone, and Povidone. PVP is widely available commercially, in different levels of quality and purity. Well-known brands are for example: Kollidon™ and Luvitec™, both available from BASF or Sigma-Aldrich; Luviskol™, BASF; Periston™ BCM; and Plasdone™ from Ashland.

PVP is available in polymer sizes differing between 2.500 and 2 million Dalton in weight-averaged molecular weight of the polymer. Alternatively a PVP product can be characterised by a Fikentscher K value. This is an empirical value (referenced in DIN EN ISO 1628-1) representing the viscosity of a dilute solution of the polymer relative to that of a solvent, as a measure of the polymer's molecular weight.

Some indications of the relation between K value and the corresponding range of weight-averaged molecular weights for PVP are: K 12: 2.000-3.000; K 17: 7.000-11.000; K 25: 28.000-34.000; K 30: 44.000-54.000; K 60: 350.000-550.000; and K 90: 1.000.000-1.500.000. (V. Bühler: Polyvinylpyrrolidone excipients for pharmaceuticals, ISBN 3-540-23412-8, Springer Berlin, 2005; p. 25, Table 17).

PVP has been known since the 1930's and is widely used for a variety of purposes: in foodstuffs as a stabiliser (E1201); in technical products, e.g. in paint or glue; and in cosmetics and pharmaceuticals as a binder, thickener, emulsifier or disintegrant. It is registered in Pharmacopoeias, e.g. monograph 685 in PhEur 8.

Different embodiments of an oral vaccine according to the invention, regarding for instance its composition, volume, titre, and physical form are disclosed herein below.

During the preparation and use of the oral vaccine according to the invention several intermediary compositions will be made and used, such as premixes, more or less concentrated working solutions, rough harvests, etc. These will differ in their composition and concentrations from the complete vaccine as it is released by a manufacturer for sale and commercial use. Also the vaccine as released may require a further preparation before it is ready for administration, depending on the form in which the vaccine was marketed. In practice this means that when the vaccine is released by a manufacturer in liquid form, the vaccine may be ready for direct administration, or may require dilution, when marketed in a concentrated form. Alternatively, when the vaccine is released by the manufacturer in freeze-dried form, the vaccine may be applied as a granulate or powder. More often the freeze-dried cake will first be reconstituted with the recommended volume of an appropriate diluent, before it is ready for administration.

Therefore the embodiments and details described herein of the oral vaccine according to the invention refer to the final version of the vaccine which is ready for administration to a ruminant target.

This notwithstanding the fact that even the 'final version of the vaccine which is ready for administration to a ruminant' of the oral vaccine according to the invention, may be used for a further preparation, for instance by taking up into feed or drink to allow mass administration. As a result, those further dilutions, admixtures, etc., may bring (some elements of) the vaccine outside of the (preferred) embodiments as described herein. All this is within the scope of the invention.

The live attenuated *M. haemolytica* bacteria for use in the oral vaccine according to the invention can be obtained in different ways, either as a natural isolate, or as result from manipulation and selection in vitro, to achieve attenuation in any way that provides for their safe but efficacious use in the invention. The preferred method of attenuation is one that has a stable genetic basis in the bacterial genome; such stable mutation will not change to more or less attenuation upon the many rounds of replication that a vaccine strain of bacteria must undergo. Examples of such rounds of replication are the generation of master- and working stock supplies, next the replication during production runs, and finally the rounds of replication in the target animal to establish an effective and immunising infection. Typically the most stable mutations are the ones that have been introduced by targeted recombinant DNA techniques, and that incorporate more than a single or a few nucleotides of change.

To facilitate the marketing authorisation of the resulting vaccine in many countries of the world, such mutant bacteria should preferably not contain any foreign DNA, but in particular not contain any gene of which the expression would provide resistance to an antibiotic agent.

Preferred live attenuated bacteria of *M. haemolytica* for use in the invention are bacteria as described in Chengappa & Carter (1979, Am. J. Vet. Res., vol. 40, p. 449-450), WO 2004/064776, or that comprise a mutation in the leukotoxin operon.

More preferred are live attenuated *M. haemolytica* bacteria that express an avirulent form of the leukotoxin A protein.

In this respect: the avirulence of the *M. haemolytica* leukotoxin A protein may derive from the size of the expressed leukotoxin A protein being shorter than in a wildtype protein, or may derive from the protein not achieving post-translational activation. Either way, the bacteria expressing such avirulent leukotoxin A protein remain viable and replicative, and the expressed form of the leukotoxin A protein can still stimulate an immune response, but causes significantly less pathology than a wildtype version of the leukotoxin A. Such mutants are for example described in WO 1997/016531, and in WO 1999/015670

Therefore in an embodiment of the oral vaccine according to the invention, the live attenuated *M. haemolytica* bacteria express an avirulent form of the leukotoxin A protein.

Even more preferred are live attenuated *M. haemolytica* bacteria as described in WO 1999/015670 that comprise a deletion in the leukotoxin A gene of the nucleotides that would otherwise encode amino acids numbers 34-378 of the wildtype Leukotoxin A protein. Most preferred live attenuated *M. haemolytica* is the mutant strain of *M. haemolytica* serotype 1, as described in WO 1999/015670, named: NADC D153 ΔlktA.

In a preferred embodiment, a "ruminant" for the invention relates to any ruminant of relevance to veterinary science or to commercial farming operations. Preferably this refers to bovine, caprine, ovine or *cervine* animals.

While there is commercial farming of deer, and goats, and in particular of sheep, the economic relevance of bovine-, and in particular of cattle farming has the largest global relevance.

Therefore in an embodiment of the oral vaccine according to the invention, the ruminant is a bovine animal.

In a preferred embodiment the bovine animal is taurine cattle (*Bos taurus*), zebu cattle (*Bos indicus*), buffalo, bison, yak, or wisent.

The bovine can be of any type: dairy or beef, or parental stock for dairy- or beef type.

The inventors observed that the range wherein PVP is effective in the oral vaccine according to the invention is quite broad. Only practical limitation is that at higher concentrations of PVP, or when using PVP of types with high average molecular weight ranges, it can take more time to completely dissolve the PVP and achieve complete mixing with the other constituents.

An effective oral vaccine according to the invention can be obtained by comprising a concentration of between about 0.01 and about 10% w/v PVP in the vaccine. As described above, this refers to the final version of the oral vaccine according to the invention which is ready for administration to a ruminant.

Preferably the concentration of PVP in the oral vaccine according to the invention is between about 0.05 and about 7% w/v PVP; 0.1 and 5; 0.2 and 4; or even between about 0.3 and 3% w/v PVP, in that order of preference.

Therefore in an embodiment of the oral vaccine according to the invention, the concentration of PVP is between about 0.3 and about 3% w/v.

For the invention, a number indicated with the term "about" means that number can vary between ±25% around the indicated value; preferably: about means±20% around the indicated value, more preferably: about means±15, 12, 10, 8, 6, 5, 4, 3, 2% around the indicated value, or even: about means±1% around the indicated value, in that order of preference.

In a more preferred embodiment of the oral vaccine according to the invention, the concentration of PVP is about 1.3% w/v.

In an embodiment, the oral vaccine according to the invention comprises a suitable preservative, such as thimerosal, merthiolate, or benzoic compounds, in an amount that is effective but is also tolerated by the live vaccine microorganisms.

In one embodiment, the oral vaccine according to the invention is in liquid form. The liquid may be generally aqueous, meaning: like water, but can also be a less fluid semi-solid, e.g. as in a syrup, gel, dispersion, emulsion or paste.

When released in liquid form, the vaccine formulation will comprise a stabiliser to allow prolonged storage of the live attenuated bacteria. For example: when the liquid vaccine is intended to be stored frozen at a temperature below 0° C., the stabiliser will be a cryoprotectant, for example glycerol, to allow storage at temperatures of −20° C. or less for extended periods. Alternatively, when storing the liquid vaccine at temperatures above 0° C., a suitable liquid stabiliser may be selected, for example as described in WO 2014/140239, or U.S. Pat. No. 9,393,298.

In one embodiment, the oral vaccine according to the invention is in freeze-dried form, also known as: in lyophilised form. This form has a number of advantages over a vaccine in liquid form, as it is lighter and therefore more economical to transport. Further, a freeze-dried vaccine will usually not require to be kept frozen, but can be stored at a more economical 2-8° C.

Procedures for freeze-drying are well-known to persons skilled in the art, and equipment for freeze-drying at a variety of scales is available commercially.

Therefore in an embodiment of the oral vaccine according to the invention, the vaccine is in freeze-dried form.

The oral vaccine in freeze-dried form according to the invention can be administered as such to a ruminant, for example as a fast-melt dosing-form, or as a ground powder from freeze-dried cake. More common is that the freeze-dried cake is first reconstituted in a diluent and then is ready for administration to a ruminant.

The "freeze-dried form" will be a freeze dried cake which itself can be in any form, for example as a layer in a bottle, as a tablet, or as a spherical object, for example a lyosphere as described in EP 799.613.

Typically such freeze-dried cakes will be stored in moisture-proof packaging, such as under vacuum or under nitrous gas in a sealed glass bottle, or packaged in sheet-metal or metal-laminated packaging.

Typically freeze-dried vaccines will contain a freeze-drying stabiliser that will protect the live-attenuated micro-organisms in the vaccine from decay over time in storage, but also during the cooling- and heating cycles of the freeze-drying process itself. Well-known freeze drying stabilisers contain a bulking agent such as an amino acid, e.g. glycine or arginine; a specific protein such as bovine serum albumin or a hydrolysate e.g. NZ amine; and/or polymers such as dextrane or gelatine.

In an embodiment the oral vaccine in freeze-dried form according to the invention comprises sucrose as a freeze-drying stabiliser. Not only does this provide good stabilisation, but an additional advantage is that its sweet taste makes the ingestion of the oral vaccine more pleasant to the ruminant, which helps to further reduce the stress of the vaccination for the ruminant animal.

Therefore in an embodiment of the oral vaccine in freeze-dried form according to the invention, the vaccine comprises sucrose.

The sucrose is present in the oral vaccine in freeze-dried form according to the invention in a concentration of between about 1 and about 20% w/v of the vaccine ready to use; preferably between about 2 and about 15%, between about 3 and about 10, or even between about 4 and about 8% w/v of the vaccine ready to use, in that order of preference.

More preferred, the oral vaccine in freeze-dried form according to the invention comprises sucrose in a concentration of about 6% w/v.

In addition, the oral vaccine in freeze-dried form according to the invention may comprise further excipients, for example carry-over compounds from the culture medium of the micro-organism(s) in the vaccine. For the *M. haemolytica* of the invention, that may be residues of the bacterial culture medium comprising yeast extract, dextrose, peptone, etc. Such compounds may even be helpful in the stabilisation, as additional bulking agent.

To reconstitute a freeze-dried vaccine, it is common to re-suspend the freeze-dried cake in a physiologically acceptable diluent. This is commonly done shortly before administration to the target, to ascertain the best quality of the vaccine. The diluent is typically aqueous, and can e.g. be sterile water, or a physiological salt solution.

The diluent may comprise further excipients, such as a stabiliser, or an adjuvant.

The diluent for the oral vaccine in freeze-dried form can be supplied in a separate container, either with- or separate from the freeze-dried vaccine. When provided together, the freeze-dried vaccine and the diluent (each in their own container) form a kit of parts that embodies the oral vaccine according to the invention.

Therefore in an embodiment of the oral vaccine in freeze-dried form according to the invention, the vaccine is a kit of parts with at least two containers, one container comprising the freeze-dried vaccine, and one container comprising a diluent.

In an embodiment, the oral vaccine according to the invention comprises a colorant. This can facilitate the administration, by serving as an optical indication of which ruminants have already been vaccinated. Such a colorant will of course need to be pharmaceutically acceptable, such as e.g. a food-colorant. Also the colorant needs to be non-toxic for the live attenuated *M. haemolytica* bacteria, and for any other micro-organisms, antigens, or biologically active molecules that may be included.

In an embodiment of the oral vaccine according to the invention, the vaccine comprises a blue colorant, e.g. FD&C Blue No. 1 (E133).

The colorant for the invention can be comprised in the vaccine that is released by a manufacturer, either when in liquid, semi-solid, or when in freeze-dried form.

In an embodiment of the oral vaccine in freeze-dried form according to the invention, the colorant is comprised in the diluent that is recommended by the manufacturer for the reconstitution of the freeze-dried cake, and which may be provided together with or separate from the freeze-dried vaccine, e.g. in a kit of parts.

The oral vaccine according to the invention comprises an amount of live attenuated *M. haemolytica* bacteria that is immunologically effective.

For the invention "immunologically effective" means an amount of live attenuated *M. haemolytica* bacteria that is capable of inducing in the ruminant target a protective immune response that is capable of reducing the consequences of an infection with a pathogenic *M. haemolytica* bacterium; in particular, that is an aid in the reduction of respiratory disease caused by *Mannheimia haemolytica*. A skilled person in the field of the invention will be more than capable of determining the effectiveness of an oral vaccine according to the invention, e.g. by monitoring the immunological response following vaccination or after a challenge infection, e.g. by monitoring the targets' signs of disease, clinical scores, or by re-isolation of the pathogen, and comparing these results to a vaccination-challenge response seen in mock-vaccinated animals.

Ways to determine the number of bacteria in a sample are well-known in the art. For bacteria that can form colonies on agar plates, the preferred method is by plating-out serial dilutions of the sample on suitable agar plates, incubating those under suitable conditions (e.g. regarding time, temperature, humidity, presence of oxygen, etc.), and counting of the colonies that have formed. When required a (counter-)staining may be applied to increase visibility. From this the titre of the bacteria in the original sample can be calculated. Consequently such a titre is expressed in: colony forming units (CFU). *M. haemolytica* can for instance be counted by streaking on agar plates of tryptic soy broth (TSB), and by incubation for 16-24 hours at about 36° C.

The inventors were surprised to learn that the use of PVP in an oral vaccine according to the invention, makes that the titre of *M. haemolytica* bacteria per animal dose that is required for effective protection by oral route, is now in the range of about 10^8 CFU/dose or less; this for the first time makes the economic production of an oral vaccine of *M. haemolytica* feasible.

Therefore in an embodiment, the oral vaccine according to the invention comprises at least about 1×10^7 CFU of live attenuated *M. haemolytica* bacteria as described for the invention, per animal dose of the final version of the vaccine which is ready for administration to a ruminant target.

Preferably the oral vaccine comprises at least about 3×10^7 CFU of live attenuated *M. haemolytica* bacteria per animal dose. More preferably at least about 5×10^7, 6×10^7, 7×10^7, 8×10^7, 9×10^7, 1×10^8, 2×10^8, 3×10^8, 4×10^8, 4×10^8, 5×10^8, 6×10^8, or even at least about 7×10^8 CFU of live attenuated *M. haemolytica* bacteria as described for the invention, per animal dose, in that order of preference.

More preferred, the oral vaccine according to the invention comprises between about 1×10^8 and about 7×10^8 CFU of live attenuated *M. haemolytica* bacteria as described for the invention, per animal dose. Such a dose range of *M. haemolytica* bacteria is immunologically effective, can be economically produced, and provides sufficient margin for losses in titre during production, formulation and storage.

The volume of one animal dose of the oral vaccine according to the invention is a volume that is practicable from the viewpoint of the manufacturer and of the user, such as a veterinarian or animal caretaker. In addition the volume of what constitutes one animal dose can be dependent on the type and the age of the ruminant target that is to be vaccinated. As described, the volume of one animal dose refers to the final version of the oral vaccine which is ready for administration to a ruminant target. Also the volume of a dose refers to the vaccine when in liquid form, or to the freeze-dried cake resulting from such a volume.

In an embodiment of the oral vaccine according to the invention, the volume of one animal dose is between about 0.1 and about 10 ml.

Preferably the volume of one animal dose is between about 0.2 and about 8 ml; more preferably between about 0.5 and about 6 ml; between about 0.7 and about 4 ml; or even between about 1 and about 3 ml, in that order of preference.

More preferred, the volume of one animal dose is about 2 ml.

Although it is possible to release commercial ruminant vaccines in packaging for a single animal, that is not very cost efficient, nor is it practicable for use on large number of animals. Therefore commercial forms of packaging of ruminant vaccines can be in containers that comprise the animal doses for 2, 5, 10, 20, 25, 50, 100, 200, 250, 500, or even 1000 animals. For example, a container of oral vaccine according to the invention for 50 animal doses, may contain a freeze-dried pellet of an original volume of about 30 ml of vaccine formulation. This can be dissolved in 100 ml diluent to provide 50 doses of 2 ml each.

The inventors have found that different types of PVP can be used to achieve the advantageous effect of the invention, for example they have used PVP of types such as K 12 and K 60. The K value being an indication of the weight-averaged molecular weight of the polymer, determined by viscosity measurement, as described above. Also combinations of types of PVP have been tested, such as the combination of K 12 and K 60 types, and found to be effective. Consequently, the PVP to be used for the invention can be made up of a single type of PVP, but can also be a combination of types of PVP, e.g. of two, three, or even more types.

Therefore in an embodiment of the oral vaccine according to the invention, the PVP is of a combination of types of PVP.

For the invention the "type" of PVP refers to the size class of the weight-averaged molecular weight of the PVP polymer that is being used. Such a size class can be indicated by a certain size-averaged molecular weight or -weight-range, or by the K value.

In an embodiment of the oral vaccine according to the invention, the type of PVP is one or more selected from the group consisting of: K 12, K 17, K 24, K 25, K 30, K 60, K 70, K 80, K 90 and K 120.

These different types of PVP are commercially available from a variety of suppliers. They are also available in a variety of qualities and purities. The use of PVP of a pharmaceutical grade is preferred.

The type of PVP as indicated by its K value may be written in different layouts, such as e.g. K 60, K60, K-60, etc. All these are within the scope of the invention.

Surprisingly it was found that the use of PVP provided advantages also in the formulation phase of the oral vaccine according to the invention; specifically in the freeze-drying process. For example: PVP K 12 was found to provide for improved survival of *M. haemolytica* bacteria in the freeze-drying process.

Further: PVP K 60 was found to improve the efficiency of the freeze-drying process, such that less time was needed to complete a full freeze-drying cycle In addition, PVP K 60 was found to improve the shelf-life stability of *M. haemolytica* bacteria in the oral vaccine in freeze-dried form according to the invention.

Therefore in an embodiment of the oral vaccine according to the invention, the type of PVP is K 12, or the type of PVP is K 60, or the type of PVP is a combination of K 12 and K 60.

An example of a way to combine more than one type of PVP in the oral vaccine according to the invention, is by incorporating one or more types of PVP into the culture medium during the production stage, and adding one or more further types at the stage of final formulation, or via a diluent. The PVP in the culture medium is then carried-over with the bacteria and the medium into the vaccine, when these bacteria are harvested for the subsequent formulation. In the preparation of the oral vaccine according to the invention, significant amounts of the culture medium can be taken up into the vaccine, e.g. 20% or more of the culture volume.

The oral vaccine according to the invention can advantageously be combined with one or more other antigens, micro-organisms or biologically active molecules, into a combination vaccine. However the combination needs to be made with care to safeguard the viability of the replicative vaccine components, and the stability and efficacy of the overall combination vaccine. Such choices are within the routine capabilities of the skilled person.

Therefore, in an embodiment the oral vaccine according to the invention comprises at least one additional immunoactive component.

An "additional immunoactive component" may be an antigen, micro-organisms or a part thereof, a biologically active molecule, an immune enhancing substance, and/or a vaccine, either of which may comprise an adjuvant. The additional immunoactive component when in the form of an antigen may consist of any antigenic component of veterinary importance. Preferably the additional immunoactive component is based upon, or derived from, a further micro-organism that is pathogenic to a ruminant animal. It may for instance comprise a biological or synthetic molecule such as a protein, a carbohydrate, a lipopolysaccharide, a nucleic acid encoding a proteinaceous antigen. Also a host cell comprising such a nucleic acid, or a live recombinant carrier micro-organism containing such a nucleic acid, may be a way to deliver or express the nucleic acid or an additional immunoactive component. Alternatively the additional immunoactive component may comprise a fractionated or killed micro-organism such as a parasite, bacterium or virus, or a part thereof, such as an extract, fraction, or sonicate.

The additional immunoactive component(s) may also be an immune-enhancing substance e.g. a chemokine, or an immunostimulatory nucleic acid. Alternatively, the vaccine according to the invention, may itself be added to a vaccine, while assuring viability and efficacy.

Preferred additional immunoactive components are based on, or derived from, micro-organisms that are pathogenic to ruminants. Examples of such micro-organisms are:

For cattle: *Neospora* spec., *Dictyocaulus* spec., *Cryptosporidium* spec., *Ostertagia* spec., bovine rotavirus, bovine viral diarrhoea virus, bovine coronavirus, infectious bovine rhinotracheitis virus (bovine herpes virus 1), bovine paramyxo virus, bovine parainfluenza virus, bovine respiratory syncytial virus, rabies virus, bluetongue virus, *E. coli, Salmonella* spec., *Staphylococcus* spec., *Mycobacterium* spec., *Brucella* spec., *Clostridia* spec., *Pasteurella* spec., *Mannheimia* spec., *Haemophilus* spec., *Leptospira* spec., and *Fusobacterium* spec.

For sheep and goats: *Toxoplasma gondii*, peste des petit ruminant virus, bluetongue virus, Schmallenberg virus, *Mycobacterium* spec., *Brucella* spec., *Clostridia* spec., *Coxiella* spec., *E. coli, Chlamydia* spec., *Clostridia* spec., *Pasteurella* spec., and *Mannheimia* spec.

For cervines: Epizootic haemorrhagic disease virus, bluetongue virus, papilloma virus, *Borrelia burgdorferi, Mycobacterium bovis*, and *Trueperella pyogenes.*

Preferred micro-organisms pathogenic to ruminants are one or more selected from the group consisting of: *Pasteurella multocida, Mycoplasma bovis, Histophilus somni*, bovine coronavirus, parainfluenza-3 virus, bovine respiratory syncytial virus, bovine viral diarrhoea virus, and bovine herpes virus 1.

More preferred micro-organisms pathogenic to ruminants are live attenuated *Pasteurella multocida* bacteria.

Therefore in an embodiment of the oral vaccine according to the invention, the at least one additional immunoactive component are live attenuated *Pasteurella multocida* bacteria.

Preferred live attenuated *P. multocida* bacteria for the invention, are those that are acapsular, meaning that the bacterium cannot express its normal capsule of hyaluronic acid.

The acapsular phenotype may result from any mutation in the *P. multocida* genomic locus for capsule biosynthesis. For example in the region encoding one of the transporters of polysaccharide to the surface; in the region encoding one of the hya genes; or in the region encoding proteins involved in phospholipid substitution; see: Chung et al. (1998, FEMS Microbiol. Letters, vol. 166, p. 289-296). Either way, the acapsular *P. multocida* bacteria remain viable and replicative, and can still stimulate an immune response, but cause significantly less pathology than capsular *P. multocida* can.

Therefore in an embodiment of the oral vaccine comprising live attenuated *P. multocida* bacteria as additional immunoactive component according to the invention, the live attenuated *P. multocida* bacteria are acapsular.

Even more preferred are live attenuated *P. multocida* as described in WO 2005/003330 that comprise a deletion of all or part of the hyaE gene.

Most preferred live attenuated *P. multocida* is the mutant strain of *P. multocida* serotype A3, as described in WO 2005/003330, named: 1062 ΔhyaE.

An oral vaccine according to the invention can be used either as a prophylactic- or as a therapeutic treatment, or both, as it interferes both with the establishment and with the progression of an infection by a pathogenic *M. haemolytica.*

Further or additional embodiments of the oral vaccine according to the invention are conceivable, and are perfectly achievable for a skilled person. Also these further embodiments may be applied in one or more combination(s) to the embodiments already described.

Therefore in an embodiment of an oral vaccine according to the invention, one, more, or all of the conditions apply, selected from the group consisting of:

the live attenuated *M. haemolytica* bacteria express an avirulent form of the leukotoxin A protein,
the live attenuated *M. haemolytica* is the mutant strain of *M. haemolytica* serotype 1, as described in WO 1999/015670, named: NADC D153 ΔlktA,
the ruminant is bovine, caprine, ovine or *cervine,*
the ruminant is a bovine animal,
the bovine animal is taurine cattle (*Bos taurus*), zebu cattle (*Bos indicus*), buffalo, bison, yak, or wisent,
the oral vaccine comprises a colorant,
the concentration of PVP is between about 0.3 and about 3% w/v,
the concentration of PVP is about 1.3% w/v,
the PVP is of a combination of types,
the type of PVP is one or more selected from the group consisting of: K 12, K 17, K 24, K 25, K 30, K 60, K 70, K 80, K 90 and K 120,
the type of PVP is K 12, or the type of PVP is K 60, or the type of PVP is a combination of K 12 and K 60,
the oral vaccine comprises at least about 1×10^7 CFU of live attenuated *M. haemolytica* bacteria per animal dose,
the oral vaccine comprises between about 1×10^8 CFU about 5×10^8 CFU of live attenuated *M. haemolytica* bacteria per animal dose,
the volume of one animal dose is between about 0.1 and about 10 ml,
the volume of one animal dose is about 2 ml,
the oral vaccine also comprises at least one additional immunoactive component,
the additional immunoactive component is based on, or derived from, micro-organisms that are pathogenic to ruminants,
the micro-organisms that are pathogenic to ruminants are live attenuated *Pasteurella multocida* bacteria,
the live attenuated *P. multocida* bacteria are acapsular,
the live attenuated *P. multocida* is the mutant strain of *P. multocida* serotype A3, as described in WO 2005/003330, named: 1062 ΔhyaE,
the oral vaccine is in freeze-dried form,
the oral vaccine in freeze-dried form comprises sucrose,
the oral vaccine in freeze-dried form comprises sucrose in a concentration of about 6% w/v,
the oral vaccine in freeze-dried form is a kit of parts with at least two containers, one container comprising the freeze-dried vaccine, and one container comprising a diluent, and the oral vaccine in freeze-dried form comprises a colorant comprised in the diluent.

In an embodiment of the oral vaccine according to the invention, the live attenuated *M. haemolytica* is the mutant strain of *M. haemolytica* serotype 1, as described in WO 1999/015670, named: NADC D153 ΔlktA; the ruminant is cattle; the concentration of PVP is about 1.3% w/v; the type of PVP is a combination of K 12 and K 60; the oral vaccine comprises between about 1×10^8 and about 7×10^8 CFU of live attenuated *M. haemolytica* bacteria per animal dose; the oral vaccine additionally comprises a live attenuated *P. multocida* which is the mutant strain of *P. multocida* serotype A3, as described in WO 2005/003330, named: 1062 ΔhyaE; the oral vaccine is in freeze-dried form; and comprises sucrose in a concentration of about 6% w/v.

The oral vaccine according to the invention can be prepared from live attenuated *M. haemolytica* bacteria, by methods well known in the art, and within the routine capabilities of a person skilled in the art. For example: *M. haemolytica* is cultured in fermenters using standard culture medium, e.g. TSB, with monitoring of temperature and use of variable stirrer speed and oxygen level. The complete culture is harvested at an appropriate time, such as upon reaching a specified culture density, measurable e.g. by optical density. The bacteria are then harvested for example by centrifugation, and are taken up into a pharmaceutically acceptable carrier such as water for injection combined with the necessary stabilisers.

Next an amount of PVP is added, which is gently stirred and given sufficient time to fully mix. This may take significant time; for example in experiments employing 1.3% PVP K 60 from a 45% liquid stock, it could take up to 24 hours of stirring at room temperature to have the PVP fully mixed into the other liquids.

Conveniently, the PVP can be added as a sterilised stock solution. Next the vaccine product is apportioned into appropriate sized containers, and can be further formulated such as by freeze-drying, or the product can be released on the market in liquid or semi-solid form.

The various stages of the manufacturing process are monitored by adequate tests, for instance by microbiological and immunological tests for the quality and quantity of the bacteria or any further antigens; by tests for absence of extraneous agents; and ultimately by in vitro or in vivo experiments to determine vaccine efficacy and -safety. All these are well known to a skilled person, and are prescribed in Governmental regulations such as the Pharmacopoeia, and in handbooks such as: "Remington: the science and practice of pharmacy" (2000, Lippincot, USA, ISBN: 683306472), and: "Veterinary vaccinology" (P. Pastoret et al. ed., 1997, Elsevier, Amsterdam, ISBN 0444819681).

Therefore in a further aspect the invention relates to a method for the preparation of an oral vaccine according to the invention, comprising the step of admixing live attenuated *M. haemolytica* bacteria and a pharmaceutically acceptable carrier, with PVP.

The admixing with PVP can be done in different ways, and at different times, to optimise production efficiency or vaccine characteristics.

One option is to add the PVP (either of one or of more types) to the culture of the *M. haemolytica* bacteria during the production stage, as described.

When the oral vaccine according to the invention is provided in freeze-dried form, further embodiments are possible; the PVP can be comprised in a diluent for the reconstitution of the freeze-dried cake. This diluent with PVP may be provided together with, or separate from, the freeze-dried vaccine.

However, the PVP K 60 is preferably added to the vaccine according to the invention before the freeze-drying process. This takes full advantage of the favourable effect of PVP K 60 on the efficiency increase of the freeze-drying cycle, and on the stabilisation of the *M. haemolytica* bacteria during the shelf-life.

At different points in this method, additional steps may be added, for example for additional treatments such as for purification or storage.

Next, the method for the preparation can involve the admixing with further pharmaceutically acceptable excipients such as stabilisers, carriers, adjuvants, diluents, emulsions, and the like.

As described before, an oral vaccine according to the invention can be produced in different forms, for example as a liquid, or semi-solid, and can be either a concentrate, or ready to use for administration. Alternatively, the vaccine can be formulated in a freeze-dried form. These variations, and optionally many more, can be incorporated as a further step at an appropriate point in the method for preparation according to the invention.

Therefore the method for the preparation according to the invention can comprise any of the embodiments (preferred or not) as described herein for the oral vaccine according to the invention, or any combination of two or more of those embodiments of the oral vaccine according to the invention.

The oral vaccine according to the invention, which can be made by a method for the preparation according to the invention, can be administered to a target ruminant in different ways and at a different time point in its life, as long as the efficacy and the safety are preserved. For example, as will be evident to a skilled person, it is preferred that the target ruminant did not receive around the time of vaccination e.g. via feed or as injectable, any significant amount of antibiotics to which the vaccine bacteria are sensitive.

When appropriate the ruminant target may be given a booster vaccination later in life, but preferably the oral vaccine according to the invention is administered only once per ruminant target, i.e. it is a single dose vaccine.

The oral vaccine according to the invention, in the final version of the vaccine which is ready for administration to a ruminant target, can conveniently be administered to a ruminant by administering the required volume of one animal dose, directly into the animal's mouth. Such oral administration of a fluid to an animal is commonly called a drench. Alternatively, when in semi-solid form, the oral vaccine can be orally administered as e.g. a paste or a gel. A wide variety of tools for the convenient dosing and oral administration are available commercially. Typically this will be an applicator of some sort such as a syringe or injector, with a nozzle that can be placed in the animal's mouth. Such applicators are also available for repeated administration, when treating large number of animals.

This route of administration will commonly not require the animal to be restrained, or not to the same extent as required for intranasal administration, making the oral vaccination less stressful than intranasal. Also there is no danger of the vaccine being sneezed out again. Further, in case the vaccine comprises sucrose as described, the pleasant taste facilitates the oral vaccination.

Therefore in a further aspect, the invention relates to a method for the vaccination of ruminants against respiratory disease, the method comprising the step of administering an oral vaccine according to the invention to said ruminants by oral route.

The administration regime for a method for the administration according to the invention, to a target ruminant can be in single or in multiple doses, in a manner compatible with the formulation of the vaccine and with practical aspects of the animal husbandry.

Preferably, the regime for the method for the administration according to the invention is integrated into existing vaccination schedules of other vaccines that the target ruminant may require, in order to further reduce stress to the animals and to reduce labour costs. These other vaccines can be administered in a simultaneous, concurrent, or sequential fashion, in a manner compatible with their registered use.

Therefore in an embodiment of the method for the vaccination of ruminants according to the invention, the vaccine is administered in a combination with another ruminant vaccine.

One of the advantages of the oral vaccine according to the invention is that the oral route enables the use of methods of mass administration. Such methods are without stress to the animal and are very cheap to apply.

Most prominent among those methods of mass-administration is the administration as a drink or with the feed.

Therefore in an embodiment of the method for the vaccination of ruminants according to the invention, the vaccine is administered to a target ruminant as a drink and/or with the feed.

Administration with the feed preferably regards so called top-dressing of feed, which is the addition of the vaccine to feed directly before feeding. This is advantageous to the vaccine's stability as compared to use already mixed into the feed. Alternative administrations by feeding are also: as a bait, treat, chew, or lick.

Preferred method of mass-administration of the oral vaccine according to the invention, is administration as a drink, e.g. with drinking water.

Administration via drinking water can conveniently be accomplished by using the water installations present on the farm, such as a ring-system for drinking water distribution, with drinkers which are adapted to the target animals. Essentially this would mean the dilution of the oral vaccine according to the invention in drinking water, and assuring that the animals to be vaccinated ingest the right amount of this vaccine-dilution.

To apply mass-administration of the oral vaccine according to the invention by drinking water, several practical issues need to be considered, which are all within the routine capabilities of the skilled person, such as:

the water needs to be of sufficient quality to sustain the viability of the vaccine for a sufficient amount of time, e.g. 1-2 hours until all targets have ingested their allotted amount of the vaccine-in-water dilution. In this respect, the water quality is determined both by the source of the water, or by the use of a water sanitizer.

When of insufficient quality, it may be required to rinse the water lines before adding of the vaccine, or to add a stabiliser of some sort to the water, such as skimmed milk powder at e.g. 2 grams per litre.

the dilution of the vaccine in the drinking water needs to be in a dilution that assures that each of the target animals ingests the appropriate amount of drinking water to receive (on average) a full dose of the vaccine.

the combination of the vaccine and the drinking water can be done in different ways, e.g. using a medication tank or a dosing pump; a medication tank typically contains all of the medicated water required for the treatment, and the water flow from this tank will then replace the external water flow during the time of vaccination. The use of a dosing pump implies the injection of a pre-dilution of the vaccine into the water lines, which then mixes naturally and so forms the vaccine dilution. In either format the (pre-)dilution of the vaccine needs to be carefully calculated to achieve that each animal will receive (on average) of full dose of vaccine.

to monitor vaccine distribution through the water-lines, and the uptake by the animals, a colorant can be added, in addition to what may already be present in the vaccine.

Therefore in an embodiment of the method for the vaccination of ruminants according to the invention, the vaccine is administered to a target ruminant in drinking water.

One preferred occasion for administering the oral vaccine according to the invention is in the preparation of ruminants for transport, for example to a grower- or finisher farm. Such transport and comingling is quite stressful to the ruminants, and is often followed by outbreaks of RRD in the weeks after. The timing of such vaccination can be optimised to take place at about 1-2 weeks before a planned transportation, e.g. before weaning or before transport to a feedlot farm.

Therefore, in an embodiment of the method for the vaccination of ruminants according to the invention, the vaccine is administered to a target ruminant 1-2 weeks before a planned transportation of the ruminant. Preferably such vaccination is administered via drinking.

The age, weight, sex, immunological status, etc. of the target ruminant for a vaccination according to the invention, are not critical although it is favourable to vaccinate healthy targets, and to vaccinate as early as possible to prevent (the consequences of) an early infection by a pathogenic *M. haemolytica*.

Therefore, in an embodiment of the method for the vaccination of ruminants according to the invention, the oral vaccine according to the invention is administered to young ruminants.

The term "young" refers to the period in the life of a ruminant up to its weaning. This period differs for various species of ruminants; for cattle weaning is typically at about 6-8 weeks of age, for lambs weaning is at about 4-6 weeks of age. Preferably "young" refers to 0-8 weeks of age, more preferably to 0-6 weeks of age.

Preferred method of mass-administration of the oral vaccine according to the invention, is, e.g. with drinking water.

One advantageous method for the vaccination of ruminants by the administration as a drink, according to the invention, is to administer the oral vaccine to ruminants by admixing the vaccine with milk, and feeding this mixture to the ruminants. Ruminants of all ages like to drink milk, therefore such administration is totally stress-free for the animals. This can conveniently be done by feeding an appropriate amount of vaccine-in-milk dilution to the ruminant using a drinking trough or a bucket, or for young ruminants a bottle with a suction nipple. The milk drink with the vaccine dilution can conveniently be prepared and administered to a large number of ruminants at a time.

A further advantage is that the *M. haemolytica* bacteria are quite stable in milk.

Therefore, in an embodiment of the method for the vaccination of ruminants according to the invention by administration as a drink, the oral vaccine according to the invention is admixed with milk and fed to ruminants.

The "milk" to be used for admixing with the oral vaccine according to the invention, can be whole milk, and is preferably from the same species as the target. Alternatively the milk can be prepared from powdered milk, such as a milk replacer. Commercial milk replacer is available in a variety of types, both for general cross-species use, or for species-specific use. The milk evidently needs to be of good quality, and the dilution of the vaccine in the milk is preferably prepared shortly before administration by feeding.

The feeding of the vaccine dilution in milk can be incorporated into the normal milk feeding program of the young ruminant target, the timing and the quantities of which will be dependent of its species and age.

While the dilution applied for the vaccine in milk will probably not be a great as for a drinking water administration, this still can be between about 10 and 1000 times. For example one animal dose of the oral vaccine according to the invention can conveniently be administered to a bovine calf in 1 litre of milk, representing e.g. a 1:500 subsequent dilution to a prescribed animal dose volume of 2 ml per animal.

The dilution of the vaccine in milk or in drinking water can be prepared either from the oral vaccine according to the invention itself, or from an intermediate dilution. For example the vaccine when in freeze-dried form and already containing the PVP, can be dissolved in a small volume of water or milk and subsequently in a larger volume of water or milk. Alternatively, when the vaccine in freeze dried form did not yet contain PVP, it should first be dissolved in diluent-containing PVP, and then in water or milk.

Alternative wording can be used to describe the embodiments of the oral vaccine and of the method for the vaccination of ruminants, both according to the invention:

In a further aspect the invention relates to an oral vaccine according to the invention, for administration to a ruminant as a drink or with the feed.

In a preferred embodiment, the drink is a dilution of the vaccine in milk, for administration by feeding to young ruminants.

The "milk drink" is composed and prepared as described above.

In a further aspect the invention relates to a milk drink for the vaccination by feeding of young ruminants against respiratory disease, the drink comprising a dilution of an oral vaccine according to the invention.

In a further aspect the invention relates to the use of an oral vaccine according to the invention for the manufacture of a milk drink for the vaccination by feeding of young ruminants against respiratory disease.

In a further aspect the invention relates to a method for the reduction of an infection with *M. haemolytica* or of associated signs of disease in ruminants, characterised in that the method comprises the administration to said ruminants of an oral vaccine according to the invention.

In a preferred embodiment of the method for the reduction of an infection according to the invention, the vaccine is administered to a target ruminant as a drink and/or with the feed.

The invention will now be further described by the following, non-limiting, examples.

EXAMPLES

Example 1: Efficacy Study of Oral Vaccine Against *M. haemolytica* Comprising PVP 1.1. Summary This experiment demonstrated the efficacy of an oral vaccine comprising a relatively low dose of live attenuated *M. haemolytica* in PVP, to protect bovine calves of 2 to 3 weeks of age against respiratory disease caused by a severe challenge infection with *M. haemolytica*.

Forty colostrum-deprived calves, approximately 2 weeks of age were randomized into two treatment groups. Twenty calves in group A were orally administered the test vaccine in milk replacer, containing per dose: the *M. haemolytica* strain NADC D153 ΔlktA, at about 2×10^8 CFU, and a live attenuated *P. multocida* antigen, strain 1062 ΔhyaE, at about 1×10^9 CFU. The second group of 20 calves in group B similarly received a control vaccine, containing only the live attenuated *P. multocida* antigen. Four weeks after vaccination, all animals were challenged intra-tracheally with a culture of virulent *M. haemolytica*. After a seven day observation period, which included clinical monitoring for respiratory rate per minute and rectal temperature, the animals were euthanized, necropsied and the lungs were scored for pneumonic lesions.

The data was analysed statistically to determine the differences in lung lesion scores (LLS) between the two treatment groups. The animals in vaccine group A had significantly lower LLS (mean LLS of 11.5) than those in control group B (mean LLS of 28.4); this as a result of the oral administration of the vaccine with at titre of *M. haemolytica* of 1.8×10^8 CFU/dose, demonstrating the efficacy of the PVP enhanced oral vaccine.

1.2. Vaccine

The vaccine for group A contained the *M. haemolytica* and the *P. multocida* bacteria at passage +5 from the master seed. Vaccine was reconstituted from freeze dried formulation with sterile water, to 2 ml per animal dose.

The vaccine for group B, (control group to vaccine group A) contained only the *P. multocida* bacteria. The composition of the vaccine B was the same as that for vaccine A, except that the volume of *M. haemolytica* bacteria in water/sucrose/PVP was replaced by TSB.

The *M. haemolytica* bacteria were cultured using 1% PVP K 12 in their growth medium, the whole culture was harvested, and the formulated vaccine contained 80% of its volume from bacteria and culture medium, providing 0.8% w/v of PVP K 12 to the vaccine. This was then mixed with a stabiliser containing sucrose and PVP K 60, to a final concentration of 6% sucrose and 1.3% w/v total PVP (0.8% K 12 and 0.5% K 60). This was freeze-dried according to a standard protocol, and the freeze-dried product was stored at 2-7° C. PVP K 60 was obtained from Ashland Specialty Chemicals (New Jersey, USA) as 45% w/v solution in water.

1.3. Study Design:

1.3.1. Experimental Animals:

groups A and B each contained 20 calves, all from the same source, of Holstein breed and of mixed sex. The calves had been raised colostrum-deprived, and were individually marked. The calves were healthy at the time of vaccination with no prior history of vaccination against *M. haemolytica* or *P. multocida*.

Calves were randomly assigned to one of the treatment groups, and were allowed to acclimatise for about 14 days before the vaccination. Calves were fed 2 and later 3 litres of milk replacer twice a day initially from a bottle and later from a bucket. Water was available at libitum, and age-appropriate feed was provided.

Daily veterinary monitoring for general health began when the calves arrived on site and continued throughout the study. Pre-vaccination rectal temperatures and respiratory rates were recorded for all animals on days −1 and 0, and blood samples were taken. These readings all served as confirmation on the proper performance of the trial.

Prior to challenge, the calves were co-mingled and randomly divided over pens for challenge infection. The personnel administering the challenge infection, and those performing the lung lesion scoring were blinded from the grouping codes.

1.3.2. Vaccination:

Ampules of vaccines were reconstituted in sterile water, and pooled. A dose of 2 ml per animal of the respective vaccine was mixed with about 3 litres of milk replacer shorty before feeding the milk to the calve. Bacterial titrations were done in 5 fold on the pool vaccines to confirm the average titre per animal dose.

Post-vaccination animals were observed daily; one death in control group B at 20 days post vaccination was of a cause unrelated to the experiment.

1.3.3. Challenge:

At −2, −1 and 0 days prior to challenge, rectal temperatures and respiratory rates were recorded for all calves to establish baseline parameters. On day −1 blood samples were taken.

The challenge inoculum was an active culture of virulent *M. haemolytica*, strain OSU, that had been grown in TSB with moderate agitation at 37° C., and harvested at an OD of about 0.77. Prior to challenge, the culture was diluted in sterile TSB to the approximate target dose.

All the calves were challenged on day 28 post-vaccination, by intratracheal inoculation with 30 ml of TSB containing 3×10^8 CFU virulent *M. haemolytica* bacteria. The titre in CFU was determined in 5 fold, by streaking serial dilutions on standard blood-agar plates.

Post challenge the calves were observed daily at approximately the same time of day. Rectal temperatures and respiratory rates were recorded for seven days.

During post-challenge days 1-4 several calves died, or were euthanized based on the attending veterinarian's recommendation. Necropsy was conducted on those calves, and in all cases the observation was: fibrinopurulent bronchopneumonia.

On post-challenge day 7, blood samples were taken from survivors. Next all surviving calves were euthanized, and necropsy was conducted with no identification of treatment groups. Lungs were harvested from the calves and the percentage of pneumonic versus normal lung tissue was determined, according to the procedure described by Jericho & Langford (1982, Can. J. Comp. Med., vol. 46, p. 287-292). In short: of isolated lungs, the lung-lobe areas affected (visible consolidation) are identified and noted down using a grid pattern, for both lungs, and for both the ventral and the dorsal side. Next the extent of affection of lobes is counted from the number of grids, which is then multiplied by the proportion of the total lung normally represented by that lobe. All calculated values are added, maximal score is 100

Because lung lesion scoring is quite difficult, and the lesions observed are quite variable, the scoring was conducted independently by two observers and the two scores were averaged. Tissue samples of affected lung lobes were collected for bacterial re-isolation.

1.4. Results:

1.4.1. Confirmation of Vaccine Dose:

Titration results indicated that the *M. haemolytica* titre in vaccine A was 1.81×10^8 CFU/2 ml. The *P. multocida* titre was 2×10^9 CFU/2 ml dose.

1.4.2. Lung Lesion Scores:

The analysis of the lung lesion data from all the calves showed a mean LLS of 11.46 for the vaccine group A, and a mean LLS of 28.35 for the control group B. As the ratio of these LLS (vaccine/control) is 0.4, which is below 0.5, this indicates (as described in Example 3) that the challenge-protection was efficacious.

1.4.3. Clinical Observations:

With respect to the rectal temperatures of all the calves, there were 13 of the 19 animals from the control group B and 15 of the 20 animals from the vaccinated group A with a temperature >40° C. on at least one post-challenge day.

With respect to the respiration rates of all the calves, there were 14 of the 19 animals from the control and 19 of the 20 animals from the vaccinated group with a respiratory rate >40/min on at least one post-challenge day.

Both these readings confirm the proper execution of this vaccination-challenge trial.

1.4.4. Mortality Analysis:

During the post-challenge period, 10 of the 19 animals from the control group B, and 5 of the 20 animals from the vaccine group A died, indicating that the challenge was severe. Clearly, significantly fewer calves died in the vaccinated group A, compared to the control group B.

1.4.5. Bacterial Isolation:

Out of the 39 lung tissue samples from which isolation was attempted, growth was observed from 37 samples. Eighteen positive isolations were from the vaccine group A and 19 from the control group B. All positive samples were identified as *M. haemolytica*.

1.5. Conclusions:

Cattle vaccinated orally at 2 weeks of age with a live attenuated *M. haemolytica* vaccine with PVP, and subjected to a severe challenge with pathogenic *M. haemolytica* 4 weeks later, had significantly reduced lung lesion scores, as compared to calves that received a control vaccination before challenge.

The oral vaccine comprised *M. haemolytica* at 1.81×10^8 CFU and 1.3% w/v total PVP per animal dose of 2 ml, and was administered in 3 litres of milk-replacer.

The data proves that the vaccine complies with the indication: "For the oral vaccination of healthy cattle, 2 weeks of age or older, as an aid in the reduction of respiratory disease caused by *Mannheimia haemolytica*."

Example 2: Collected Results of Studies on Oral Vaccines Against *M. haemolytica* with/without PVP Prior to the experiments described in Examples 1 and 2, several earlier vaccination-challenge studies had been performed in calves. These tested several oral vaccines, comprising different amounts of live-attenuated *M. haemolytica*, but without PVP. Those experiments were generally performed as described in Example 1.

The common result was that only when very high doses of a live attenuated strain of *M. haemolytica* were applied, then effective protection against challenge could be achieved, and lower doses were not protective.

It was only after the introduction of PVP into the vaccine, that lower doses of *M. haemolytica* also became effective.

The combined results of a representative set of these experiments are presented in Table 1 below, which focuses on the relative reduction of lung-lesions, as the most important parameter of effective protection against a challenge with pathogenic *M. haemolytica*.

TABLE 1

Combined results of M. haemolytica vaccination-challenge experiments in calves.

| | Oral vaccine | | Average lung lesion scores | | | Chall.-prot. |
|---|---|---|---|---|---|---|
| exp. nr. | M. haem dose | PVP used | Vaccinates (%) | Controls (%) | Ratio V/C | to M. haem. |
| 029 | 1,5 × 10^10 | No | 8,0 | 17,6 | 0,45 | Yes |
| 031A | 1,1 × 10^8 | No | 7,1 | 9,0 | 0,79 | No |
| 034B | 7,4 × 10^7 | No | 3,5 | 3,9 | 0,90 | No |
| 031B | 5,1 × 10^7 | No | 6,8 | 9,0 | 0,76 | No |
| Expl. 1 | 1,8 × 10^8 | 1.3 % | 11,5 | 28,4 | 0,40 | Yes |

Indications used in Table 1: 'exp.nr'=experiment number; 'M. haem dose'=dose/animal of live attenuated *M. haemolytica* bacteria in the oral vaccine; 'Chall.-prot. to M. haem.'=protection against *M. haemolitica* challenge; 'Expl. 1' refers to the experiments described in Example 1.

To facilitate the interpretation of the relative reduction of lung-lesions, the ratio is indicated of the lung lesion scores of the vaccinates over that of the controls ('Ratio V/C'). This is a simplification of the advanced statistical analysis that was applied in these experiments. Nevertheless this ratio gives a quick indication of protection: when this ratio is 0.5 or less, the test animals can be considered protected against a severe challenge with pathogenic *M. haemolytica.*

Table 1 clearly illustrates the advantageous effects of the use of different concentrations of PVP, in an oral vaccine for ruminants against pathogenic *M. haemolytica.*

Also a further comparison was made between groups from the experiments described herein in Examples 1 and 2, that did or did not receive PVP added to the vaccine. Specifically: a group receiving vaccine with PVP from Example 1 was compared to a group without PVP from the studies listed in Table 1, both for a vaccine dose of 1×10^8 CFU/dose. Other circumstances were the same: vaccine was administered orally in 1 litre of milk replacer, and challenge dose was 2×10^8 CFU/ml at 30 ml challenge dose.

The effect of vaccination on challenge-induced lung scores was compared to unvaccinated controls for both these groups. The comparison demonstrates an impressive improvement is reached upon the addition of PVP, namely: without PVP, a vaccination improves lung scores by 21% as compared to unvaccinated controls; whereas with 1.3% PVP added, vaccination (with the same dose of bacteria) improves lung scores by 62%, relative to controls. Consequently, the addition of PVP improves the protective effect of vaccination on lung scores by 3 fold !

Example 3: Duration of Immunity Trial

This experiment is currently in progress and will confirm the duration of the immunity induced by the oral vaccine according to the invention.

The layout of this experiment is largely the same as that described in Example 1:

At least 40 colostrum deprived calves, two to three weeks of age, will be randomized into two treatment groups of 20 each. One group (group A) will be orally administered a 2 ml dose of the oral vaccine mixed with whole milk or milk replacer (about 3 litres) containing the live attenuated *M. haemolytica* at a titre of about 1.8×10^8 CFU/dose, and *P. multocida* bacteria at about 2.3×10^8 CFU/dose. The vaccine comprises 1.3% w/v total PVP (K 60 and K 12), and a blue colorant, and was freeze-dried with 6% sucrose. The control group B will receive the same vaccine, orally, in milk, but will comprise only *P. multocida* bacteria.

Four months after vaccination, the animals will be commingled and challenged intra-tracheally with a culture of virulent of *M. haemolytica*. After a seven day observation period, the animals will be euthanized, necropsied and scored for pneumonic lesions. The data will be analysed statistically to determine the differences in lung lesion scores between the two treatment groups.

This study will demonstrate that a 4 month duration of immunity can be obtained with the oral vaccine according to the invention.

Example 4: Duration of Immunity Trial, as Performed 4.1. Introduction:

This study is the completion of the experiment already described as Example 3 above. The purpose of this study was to demonstrate the sustained efficacy of the *M. haemolytica* vaccine according to the invention, at four months after oral administration to 2 week old calves, against respiratory disease caused by *M. haemolytica*. The vaccine used was a modified live vaccine containing the *M. haemolytica* strain NADC D153 ΔlktA, which was formulated with 1.3% w/v total PVP (K 60 and K 12), as described above in Examples 1 and 3. The vaccine for group A contained live attenuated bacteria of both *M. haemolytica* and of *P. multocida*; the control vaccine for group B only contained live attenuated *P. multocida.*

The calves were received in two shipments, combined, and randomised over the two treatment groups: 21 in group A (vaccinates) and 20 in group B (controls). 4 months after vaccination the calves were given a challenge infection, and one week after challenge the calves were euthanized and the lungs were evaluated and scored for pneumonic lesions.

4.2. Materials and Methods 4.2.1. Animals and Housing

The calves were received in two shipments of 24 and 20 calves, Within each shipment, calves were randomly assigned to the two treatment groups using the RAND function in Excell™. All calves were from the same source and no blocking factors were used. The calves in the two treatment groups were housed separately in individual huts. After two months they were moved to a different building, and housed separately in pens based on the treatment groups, whereby comparable numbers of vaccinates and controls were in each building. The calves were commingled prior to challenge, and remained commingled until the end of the study.

The personnel who administered the challenge, performed lung lesion scoring, and bacterial isolation from lung tissues, were blinded to the study grouping codes.

The calves were of both sexes, and were colostrum deprived Holstein race. Identification was by ear tags, and all animals were healthy at the time of vaccination with no prior history of vaccination against *M. haemolytica*.

The calves were bottle-fed at least 2 liters of milk replacer twice a day during the first week of life. From the second week onwards, the calves were bucket-fed at least 2.5 liters of milk replacer twice a day till they were approximately 8 weeks old. Water was provided ad libitum. Post-weaning, they received standard feed for animals of this age.

All calves were allowed to acclimate for at least 13 days prior to vaccination. All animals were under daily observation by a veterinarian and animal caretakers.

4.2.2. Vaccine

The vaccine for group A was a lyophilized sample containing the *M. haemolytica* NADC D153 ΔlktA strain. Also vaccine A contained an acapsular mutant strain of *Pasteurella multocida*, strain 1062 with ΔhyaE mutation. One dose of vaccine A contained about 1.8×10^8 CFU per 2 mL dose of *M. haemolytica*, and about 1×10^9 CFU per 2 mL dose of *P. multocida*. Both bacteria were at the $5^{th}$ passage level from their master seed.

The vaccine for control group B did not contain the *M. haemolytica*, but contained the *P. multocida*, and was otherwise prepared similarly to vaccine A. For both vaccines the Blushadow™ diluent was used for rehydrating the lyophilized vaccines.

For each target, a 2 ml sample was taken from pools of vaccine A or vaccine B, dependent on the planned treatment. This was mixed with approximately 2.5 liters of milk replacer, which was fed completely to the calf, as a single dose. The vaccine pools were back-titrated to verify the dose actually applied.

Animals were observed daily for general health and observations recorded. During the post-vaccination period, some animals died due to causes unrelated to the experiment. During the experiment and surrounding treatment steps, blood samples were taken, and rectal temperatures and respiratory rates were noted down.

4.2.3. Challenge

The challenge material was an active culture of virulent *M. haemolytica* (strain OSU), which was grown in Tryptic soy broth with moderate agitation at 37° C. Prior to challenge, the culture was diluted in sterile TSB to the approximate target dose, which was based on a prior established correlation between the OD value and CFU counts.

The challenge was administered on day 123 post-vaccination. Each calf in the study was inoculated once intratracheally with 40 mL of TSB containing at least 1×10^8 virulent *M. haemolytica* bacteria.

This challenge dose was determined by standard bacterial titration in 5-fold of the challenge material used.

After challenge the calves were observed daily at approximately the same time of day. Rectal temperatures and respiratory rates (per minute) were recorded daily for seven days after the challenge (post-challenge days 1 through 7). Coughing, if observed and abnormal respiratory patterns, were recorded. Calves were also observed for general health and signs of any disease.

Following challenge 5 calves in group B died from 'pneumonia', that was found to be resulting from the challenge infection.

On day 7 post-challenge, all surviving calves were euthanized. Necropsy was conducted and lungs were harvested from the calves. The percentage of pneumonic lung tissue was evaluated and percent (score) of lung lesions was calculated according to the procedure described by Jericho and Langford (Can. J. Comp. Med, 1982, vol. 46, p. 287-292). Lung lesion scoring was conducted independently by two observers and the two scores were averaged.

Titration of bacteria in vaccine pools was done on tryptic soy agar plates. Serial tenfold dilutions of Vaccines A and B were made in sterile TSB. Each dilution was streaked on five plates. Plates were incubated at 36° C. for 16-24 hours. Colonies of *M. haemolytica* could be counted directly; plates of *P. multocida* required a further incubation at room temperature for an additional 16-24 hours. The plates for counting *M. haemolytica* contained 0.001% Nafcillin to inhibit the growth of *P. multocida*; the plates for counting *P. multocida* contained 0.0015% Potassium tellurite to inhibit the growth of *M. haemolytica*.

Titration of the *M. haemolytica* challenge material was on standard blood-agar plates.

4.3. Results 4.3.1. Confirmation of Vaccine Dose

Titration results indicated that vaccine A contained 1.64×10^8 *M. haemolytica* per 2 mL dose.

4.3.2. Confirmation of Challenge Dose

Titration results indicated that each animal in the study received approximately 4.06×10^8 *M. haemolytica* organisms in the 40 mL dose administered by the intra-tracheal route.

4.3.3. Mortality Analysis:

The percent death caused by the *M. haemolytica* challenge was evaluated by the prevented fraction (PF) method and 95% confidence interval for the PF. The PF and associated confidence intervals were calculated with SAS™ 9.3 using the procedure BINOMIAL from StatXact 10 Procs for SAS.

During the post-challenge period, 5 of the 15 animals from the control group died. There were no deaths in the vaccinated group after challenge. The prevented fraction was 1.00, with a lower 95% highest density confidence bound of 0.5.

4.3.4. Lung Lesion Scores:

The percent of lung tissue with lesions caused by *M. haemolytica* infection was evaluated by the mitigated fraction (MF) method with associated 95% highest density confidence interval. The MFs and associated confidence intervals were calculated with SAS™ 9.3 using the procedure PROC_R with R module.

The analysis of the data showed that the mean LLS for the control group B was 24.32 and the mean LLS for the vaccinated group A was 1.02. The mitigated fraction was 0.74 with a lower 95% highest density confidence bound of 0.5.

4.3.5. Clinical Observations:

With respect to the rectal temperatures of all the calves, there were 5 of the 15 animals from the control group B and 3 of the 18 animals from the vaccinated group A with a temperature of over 40° C. on at least one post-challenge day.

With respect to the respiration rates of all the calves, there were 10 of the 15 animals from the control group B, and 4 of the 18 animals from the vaccinated group A with a respiratory rate of over 40/minute, on at least one post-challenge day.

4.4. Conclusions

During the post-challenge period, 5 of the 15 animals from the control group B died and there were no deaths in the vaccinated group A. The mortality rate was significant in the control group (p=0.0092).

Also, significant differences of lung lesion scores were observed between the two treatment groups, where control group B animals scored LLS of 24.32 and vaccinates from group A only scored LLS of 1.02 (p=0.0003). There was also a significant difference between the control and vaccinated groups with respect to the maximum respiratory rate (p=0.0063).

Consequently, the oral *M. haemolytica* vaccine according to the invention was demonstrated to be protective at a dose of 1.64x10^8 CFU/2 mL dose, given by oral route, against a severe challenge infection. The results of this experiment demonstrate convincingly the efficacy of a vaccine according to the invention in protecting calves against respiratory disease caused by *Mannheimia haemolytica* infection, even up to 4 months after vaccination. After challenge, calves in the vaccinated group A had significantly less infection and disease as indicated by their much lower scores of mortality and LLS.

Further, the difference found in the protection induced by groups A and B also convincingly demonstrates that protection against *M. haemolytica* challenge could only be provided by vaccination with *M. haemolytica*, and not by *P. multocida* vaccination.

The invention claimed is:

1. An oral vaccine against respiratory disease in a ruminant comprising live attenuated *Mannheimia haemolytica* bacteria and a pharmaceutically acceptable carrier, wherein the vaccine also comprises Polyvinylpyrrolidone (PVP); wherein the concentration of PVP is between about 0.3 and about 3% w/v.

2. The oral vaccine of claim 1, wherein the live attenuated *M. haemolytica* bacteria are unable to express a virulent leukotoxin A protein.

3. The oral vaccine of claim 2, wherein the ruminant is a bovine animal.

4. The oral vaccine of claim 3, wherein the PVP is of a combination of types of PVP.

5. The oral vaccine of claim 4, wherein the oral vaccine also comprises at least one additional immunoactive component.

6. The oral vaccine of claim 5, wherein the at least one additional immunoactive component is a live attenuated *Pasteurella multocida* bacterium.

7. The oral vaccine of claim 6, wherein the combination of types of PVP are K 12 and K 60.

8. The oral vaccine of claim 3, wherein the oral vaccine also comprises at least one additional immunoactive component.

9. The oral vaccine of claim 8, wherein the at least one additional immunoactive component is a live attenuated *Pasteurella multocida* bacterium.

10. The oral vaccine of claim 1, wherein the ruminant is a bovine animal.

11. The oral vaccine of claim 1, wherein the vaccine is in freeze-dried form.

12. The oral vaccine of claim 1, wherein the PVP is of a combination of types of PVP.

13. The oral vaccine of claim 1, wherein the oral vaccine also comprises at least one additional immunoactive component.

14. The oral vaccine of claim 13, wherein the at least one additional immunoactive component is a live attenuated *Pasteurella multocida* bacterium.

15. The oral vaccine of claim 1, wherein the PVP is a type selected from the group consisting of K 12, K 17, K 24, K 25, K 30, K 60, K 70, and combinations thereof.

16. A milk drink for vaccinating young ruminants against respiratory disease comprising a dilution of the oral vaccine of claim 1, with milk.

17. An oral vaccine against respiratory disease in a ruminant comprising live attenuated *Mannheimia haemolytica* bacteria and a pharmaceutically acceptable carrier, wherein the vaccine also comprises Polyvinylpyrrolidone (PVP); wherein the PVP is a type selected from the group consisting of K 12, K 17, K 24, K 25, K 30, K 60, K 70, and combinations thereof.

18. An oral vaccine against respiratory disease in a ruminant comprising live attenuated *Mannheimia haemolytica* bacteria and a pharmaceutically acceptable carrier, wherein the vaccine also comprises Polyvinylpyrrolidone (PVP); wherein the PVP is of a combination of types of PVP; and wherein the combination of types of PVP are K 12 and K 60.

19. A method for the preparation of an oral vaccine of claim 1, comprising the step of admixing live attenuated *M. haemolytica* bacteria and a pharmaceutically acceptable carrier, with PVP.

20. A method of vaccinating a ruminant against respiratory disease comprising the step of administering the oral vaccine of claim 6, to said ruminant by an oral route.

* * * * *